United States Patent

Kuo et al.

Patent Number: 5,476,866
Date of Patent: Dec. 19, 1995

[54] ISOXAZOLES

[75] Inventors: Elizabeth A. Kuo; Robert Westwood, both of Swindon, United Kingdom

[73] Assignee: Roussel Uclaf, France

[21] Appl. No.: 293,840

[22] Filed: Aug. 22, 1994

[30] Foreign Application Priority Data

Oct. 1, 1993 [GB] United Kingdom .................. 93202992

[51] Int. Cl.$^6$ ...................... C07D 263/30; A61K 31/42
[52] U.S. Cl. ............................................ 514/378; 548/248
[58] Field of Search ............................. 548/248; 514/378

[56] References Cited

U.S. PATENT DOCUMENTS 4,935,434  6/1990  Han ........................................ 514/378

FOREIGN PATENT DOCUMENTS

| 257882 | 3/1988 | European Pat. Off. | ............... 548/248 |
| 0326108 | 8/1989 | European Pat. Off. | ............... 548/248 |
| 573318 | 12/1993 | European Pat. Off. | ............... 548/248 |
| 2313052 | 12/1976 | France . | |

OTHER PUBLICATIONS

CA 116:128908h Isoxazole . . . antirheumatics, Bartlett et al., p. 890, 1992.
CA 112:55842n Preparation . . . antiarthritics, Han, p. 771–772, 1990.
CA 116:128908h Isoxazole–. . . antirheumatics, Bartlett et al., p. 890, 1992.

Primary Examiner—Joseph K. McKane
Attorney, Agent, or Firm—Bierman and Muserlian

[57] ABSTRACT

A compound selected from the group consisting of a compound of the formula

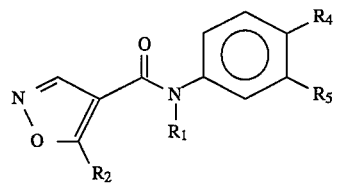

wherein $R_1$ is hydrogen or alkyl of 1 to 3 carbon atoms; $R_2$ is cycloalkyl of 3 to 6 carbon atoms; $R_4$ is selected from the group consisting of halogen, nitrile, nitro, —$SCH_3$, -alkylcarbonyl of 1 to 6 carbon atoms, cycloalkylcarbonyl of 3 to 6 carbon atoms, —$CX_3$, —$WCX_3$, —$(CH_2)_nCX_3$, —$(CX_2)_nCX_3$, —$W(CX_2)_nCX_3$ and a —$W(CH_2)_nCX_3$, in which X is halogen, W is oxygen or sulfur, and n is 1, 2 or 3; and $R_5$ is selected from the group consisting of hydrogen, alkyl of 1 to 3 carbon atoms and cycloalkyl of 3 to 6 carbon atoms; with the proviso that if $R_5$ is hydrogen, $R_4$ is not —$SCH_3$ or —$CF_3$ and their non-toxic pharmaceutically acceptable salts having anti-prolifera-tive, anti-inflammatory and anti-tumor activity.

9 Claims, No Drawings

ISOXAZOLES

STATE OF THE ART

WO91/17748 describes certain isoxazole derivatives and their use as drugs and EP-A-326,107 discloses antiarthritic β-cycloalkyl-β-oxopropionitriles and a method for their preparation. EP-A-326,108 and FR-A-2,313,031 disclose certain alkyl-substituted isoxazole derivatives and EP-A-440,503 describes isoxazole derivatives which are substituted by three different radicals and which can be used for the treatment of inflammatory diseases.

OBJECTS OF THE INVENTION

It is an object of the invention to provide the novel isoxazoles of formula I and their non-toxic, pharmaceutically acceptable salts and a process for their preparation.

It is another object of the invention to provide novel anti-inflammatory compositions and a novel method of relieving inflammation in warm-blooded animals.

These and other objects and advantages of the invention will become obvious from the following description.

THE INVENTION

The novel compounds of the invention are selected from the group consisting of a compound of the formula

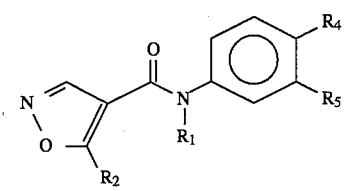

wherein $R_1$ is hydrogen or alkyl of 1 to 3 carbon atoms; $R_2$ is cycloalkyl of 3 to 6 carbon atoms; $R_4$ is selected from the group consisting of halogen, nitrile, nitro, —$SCH_3$, -alkylcarbonyl of 1 to 6 carbon atoms, cycloalkylcarbonyl of 3 to 6 carbon atoms, —$CX_3$, —$WCX_3$, —$(CH_2)_nCX_3$, —$(CX_2)_nCX_3$, —$W(CX_2)_nCX_3$ and a —$W(CH_2)_nCX_3$, in which X is halogen, W is oxygen or sulfur, and n is 1, 2 or 3; and $R_5$ is selected from the group consisting of hydrogen, alkyl of 1 to 3 carbon atoms and cycloalkyl of 3 to 6 carbon atoms; with the proviso that if $R_5$ is hydrogen, $R_4$ is not —$SCH_3$ or —$CF_3$ and their non-toxic pharmaceutically acceptable salts. The compounds of formula I can exist in all tautomeric forms.

Cycloalkyl of 3 to 6 carbon atoms includes cyclopropyl, cyclobutyl, cyclopentyl or cyclohexyl and alkyl of 1 to 3 carbon atoms includes methyl, ethyl, propyl or isopropyl. Halogen includes fluorine, chlorine, bromine or iodine.

Preferred compounds of formula I are those wherein $R_1$ is hydrogen, $R_2$ is cyclopropyl, $R_4$ is selected from the group consisting of halogen, —CN, —$NO_2$, —$CF_3$, —$C_2F_5$, —$OCF_3$ and —$SCF_3$ and $R_5$ is methyl or ethyl. More preferred compounds of formula I are those wherein $R_4$ is halogen or —$NO_3$ or —CN or —$CF_3$ and $R_5$ is methyl. Most preferred compounds of formula I are those wherein $R_4$ is bromine, chlorine, —CN or —$CF_3$ and $R_5$ is methyl or $R_4$ is —CN or —$NO_2$ and $R_5$ is hydrogen.

Specific preferred compounds of formula I are 5-cyclopropyl-N-(4-cyanophenyl)-isoxazole-4-carboxamide; 5-cyclopropyl-N-(4-nitrophenyl)-isoxazole-4-carboxamide; 5-cyclopropyl-N-(4-bromo-3-methylphenyl)-isoxazole-4-carboxamide; 5-cyclopropyl-N-(4-chloro-3-methylphenyl)-isoxazole-4-carboxamide; 5-cyclopropyl-N-(4-cyano-3-methylphenyl)-isoxazole-4-carboxamide; 5-cyclopropyl-N-(4-trifluoromethyl-3-methylphenyl)-isoxazole-4-carboxamide; and salts thereof.

The novel process of the invention for the preparation of the compounds of the formula I comprises reacting a compound of the formula

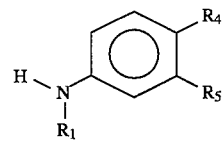

wherein $R_1$, $R_4$ and $R_5$ are as defined above with a compound of the formula

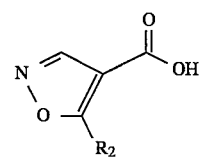

wherein $R_2$ is as defined above or a functional derivative thereof to obtain the compound of formula I.

The reaction between the compound of formula II and the compound of formula III is preferably effected in the presence of an anhydrous organic solvent such as dichloromethane or tetrahydrofuran, and in the presence of a coupling agent such as dicyclohexylcarbodiimide or diisopropylcarbodiimide at ambient temperature.

The reaction between the compound of formula II and a functional derivative of the compound of formula III is preferably effected in the presence of an anhydrous organic solvent such as dichloromethane or diethyl ether and in the presence of an organic base such as pyridine or triethylamine and at a low temperature. Where a functional derivative of a compound of formula III is used, this is preferably an acid halide, more preferably an acid chloride. An acid chloride of a compound of formula III may, for example, be prepared in situ by reaction of a compound of formula (III) with thionyl chloride or phosphorus pentachloride.

The compounds of formula II are generally known products or can be prepared by diazotization, then reduction of the corresponding nitrobenzenes by processes known per se. The nitroanilines used can be prepared as indicated, for example, in Sura et al., Synthetic Communications (1988), Vol. 18, (16–17), pp. 2161–5. Certain of the anilines of formula II can be prepared by processes described in European Patent EP-A-206,951 or by reduction of the corresponding nitrobenzenes.

The compounds of formula III used in the above process are also generally known products or may be prepared by processes described in the literature, for example in EP-A-326,107.

The anti-inflammatory compositions of the invention are comprised of an anti-inflammatorily effective amount of a compound of formula I and an inert pharmaceutical carrier. The compositions may be in the form of tablets, dragees, capsules, granules, suppositories and injectable solutions or suspensions.

Examples of excipient or inert carriers are talc, gum arabic, starch, lactose, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a remarkable anti-proliferative, anti-inflammatory and anti-tumor activity and inhibit both the inflammatory response caused by irritant agents, and delayed hypersensitivity reactions, by hindering activation of the immune cells by a specific antigen.

A further advantage is shown by the compositions of the invention wherein $R_5$ is methyl as the presence of this methyl substituent has been shown to result in compounds having a shorter metabolic half-life than the corresponding compounds without the methyl substituent; this is illustrated further in the experimental section. Accordingly, such compounds wherein $R_5$ is methyl are further examples of particularly preferred compounds of the invention.

These compositions are of use, in the treatment of tumors, rheumatoid arthritis and chronic inflammatory diseases of immune or non-immune origin (e.g. graft-versus-host disease, transplantation reactions, uveitis, psoriasis, cancer, diabetes, prevention of acute or chronic rejection post organ transplantations, re-stenosis post angioplasty).

The novel method of the invention for relieving inflammation in warm-blooded animals, including humans, comprises administering to warm-blooded animals an anti-inflammatorily effective amount of a compound of formula I and its non-toxic pharmaceutically acceptable acid addition salts. The compounds may be administered orally, rectally or parenterally and the usual daily dose is 0.001 to 3 mg/kg depending on the specific compound, the condition treated and the method of administration.

In the following examples, there are described several preferred embodiments to illustrate the invention. However, it is to be understood that the invention is not intended to be limited to the specific embodiments.

EXAMPLE 1

5-cyclopropyl-N-(4-bromo-3-methylphenyl)-isoxazole-4-carboxamide

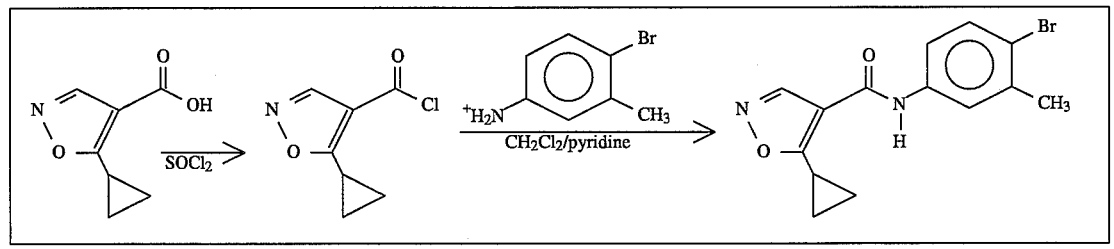

3.33 g (21.7 mmol) of 5-cyclopropylisoxazole-4-carboxylic acid and 25 ml of thionyl chloride were refluxed for 90 minutes and after the thionyl chloride was evaporated in vacuo, the residue was azeotroped twice with toluene. 4.0 g (21.7 mmol) of 4-bromo-3-methyl-aniline were dissolved in 125 ml of dry dichloromethane, cooled to 0° C. and the acid chloride and 2.4 g (30 mmol) of pyridine each dissolved in 10 ml of dichloromethane, were added dropwise simultaneously. After stirring for thirty minutes at 0° C., the reaction mixture was washed 3 times with 75 ml of brine, dried over $MgSO_4$ and the dichloromethane was removed in vacuo to yield a brown oil. Flash column chromatography (2% McOH, 98% $CH_2Cl_2$) yielded a pale brown oil which crystallized upon standing. Crystallization from ethanol/water yielded the desired product as cream needles melting at 133°–135° C.

Using the procedure of Example 1 and the appropriate aniline starting material, the following products were prepared:

EXAMPLE 2

5-cyclopropyl-N-(4-nitrophenyl)-isoxazole-4-carboxamide

EXAMPLE 3

5-cyclopropyl-N-(4-cyanophenyl)-isoxazole-4-carboxamide

EXAMPLE 4

5-cyclopropyl-N-(4-chloro-3-methylphenyl)-isoxazole-4-carboxamide

EXAMPLE 5

5-cyclopropyl-N-(4-cyano-3-methylphenyl)-isoxazole-4-carboxamide

EXAMPLE 6

5-cyclopropyl-N-(3-methyl-4-trifluoromethylphenyl)-isoxazole-4-carboxamide

Spectral data, yields, melting points, and analytical data for Examples 1 to 6 are given in Table I.

TABLE I

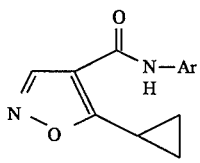

| Example | Ar | Yield % | mpt °C. | IR cm$^{-1}$ | $^1$H nmr δ | Formula m. wt. | Calc Found % C | H | N | X |
|---|---|---|---|---|---|---|---|---|---|---|
| 3 | ![]—⟨⟩—CN | 73 | 224–5 | (KBr) 3380, 3100, 3060, 2220, 1680, 1590, 1520, 1410, 1380, 1340, 1320, 1250, 1180, 1070 | δ(D$_6$DMSO) 10.40(1H, s); 9.08(1H, s); 7.87(4H, m); 2.92(1H, m); 1.22(4H, m) | C$_{14}$H$_{11}$N$_3$O$_2$ 253.26 | 66.40 66.15 | 4.38 4.41 | 16.59 16.65 | — — |
| 2 | —⟨⟩—NO$_2$ | 66 | 156–8 | 3580, 3480, 3300, 3100, 1690, 1620, 1590, 1560, 1500, 1420, 1390, 1350, 1310, 1260, 1180, 1120, 1080 | δ(D$_6$DMSO) 10.59(1H, s); 9.14(1H, s); 8.32(2H, d); 8.04(2H, d); 2.96(1H, m); 1.26(4H, m) | C$_{13}$H$_{11}$N$_3$O$_4$ 273.25 | 57.14 56.86 | 4.06 4.12 | 15.38 15.45 | — — |
| 1 | —⟨⟩—Br (with CH$_3$) | 73 | 113–5 | 3300, 1660, 1610, 1530, 1480, 1400, 1370, 1320, 1260, 1190, 1170, 1090, 1060, 1030, 1010 | δ(CDCl$_3$) 8.44(1H, s); 7.80(1H, s); 7.45(2H, m); 7.22(1H, m); 2.83(1H, m); 2.35(3H, s); 1.26(4H, m) | C$_{14}$H$_{13}$N$_2$O$_2$Br 321.17 | 52.36 52.37 | 4.08 4.13 | 8.72 8.66 | Br 24.88 Br 24.84 |
| 4 | —⟨⟩—Cl (with CH$_3$) | 61 | 127–29 | 3300, 1660, 1610, 1530, 1480, 1400, 1370, 1320, 1260, 1190, 1170, 1090, 1060, 1050 | δ(D$_6$DMSO) 10.11(1H, s); 9.09(1H, s); 7.74(1H, d); 7.60(1H, m); 7.42(1H, d); 2.97(1H, m); 2.37(3H, s); 1.23(4H, m) | C$_{14}$H$_{13}$N$_2$O$_2$Cl 276.72 | 60.77 60.47 | 4.73 4.82 | 10.12 10.12 | Cl 12.81 Cl 12.86 |
| 5 | —⟨⟩—CN (with CH$_3$) | 77 | 159–60 | 3380, 3120, 2230, 1690, 1610, 1590, 1530, 1500, 1420, 1390, 1330, 1250, 1200, 1120, 1075 | δ(D$_6$DMSO) 10.35(1H, s); 9.11(1H, s); 7.75(3H, m); 2.96(1H, m); 2.52(3H, s); 1.24(4H, m) | C$_{15}$H$_{13}$N$_3$O$_2$ 267.29 | 67.41 67.52 | 4.90 5.05 | 15.72 15.75 | |
| 6 | —⟨⟩—CF$_3$ (with CH$_3$) | 68 | 142–3 | 3340, 3080, 1890, 1760, 1680, 1600, 1540, 1480, 1450, 1400, 1370, 1320, 1250, 1180 | δ(D$_6$DMSO) 10.28(1H, s); 9.12(1H, s); 7.73(3H, m); 2.98(1H, m); 2.47(3H, s); 1.23(4H, m) | C$_{15}$H$_{13}$N$_2$O$_2$F$_3$ 310.28 | 58.07 57.58 | 4.22 4.22 | 9.03 8.90 | F 18.37 F 18.15 |

EXAMPLE 7

Tablets were prepared containing 20 mg of the Compound of Example 1 and sufficient excipient of lactose, starch, talc and magnesium stearate for a tablet weighing 150 mg.

PHARMACOLOGICAL ACTIVITY

Carrageenan rat paw oedema (Test 1)

One hour after the oral administration of the test compounds or control vehicle to groups of 6 to 12 male rats CFHB with a weight range of 160–180 g, 1 mg of carrageenan dissolved in 0.2 ml of saline was injected into the right hind foot pad. Contralateral paws received control saline injections and paw oedema responses were assessed three hours later.

Delayed-type hypersensitivity mouse paw oedema (DTH-M) (Test 2)

Groups of 8 to 10 male mice CD-1 with a weight range of 25–30 g were sensitized by the subcutaneous injection of 1 mg of methylated bovine serum albumin (MBSA) in 0.2 ml volumes of saline/Freund's complete adjuvant (FCA) emulsion. Negative control groups received injections of saline/FCA emulsion. DTH paw oedema responses were assessed twenty-four hours after the right hind foot pad challenge with 0.1 mg of MBSA in 0.05 ml volumes of saline on day seven after sensitization. Contralateral paws received control saline injections. The test compounds or control vehicles were orally administered daily on days four, five, six and twice on day seven, one hour before and six hours after MBSA challenge.

Delayed-type hypersensitivity rat paw oedema (Test 3)

Groups of 8 to 12 male rats CFHB with a weight range of 160–180 g were sensitized by the subcutaneous tail base injection with 0.1 ml volumes of FCA. Negative control groups received an injection of Freund's incomplete adjuvant. DTH paw oedema responses were assessed twenty-four hours after the right hind foot pad challenge with 0.4 mg of Mycobacterium tuberculosis extract antigen in 0.2 volumes of saline on day seven after sensitization. Contralateral paws received control saline injections. The test compounds were orally administered daily on days four, five, six and twice on day seven, one hour before and six hours after antigenic challenge. The results of these tests are given in Table II.

Doses are given in units of mg/kg p.o.

TABLE II

| | Test 1 | | Test 2 | | Test 3 | |
|---|---|---|---|---|---|---|
| Example | % inhibition | Dose | % inhibition | Dose | % inhibition | Dose |
| 1 | 12 | 50 | 41 | 100 | 24 | 50 |
| 2 | 0 | 50 | 19 | 100 | 52 | 50 |
| 3 | 43 | 50 | 43 | 30 | 60 | 10 |
| 4 | 11 | 50 | 64 | 100 | 32 | 50 |
| 5 | 18 | 50 | 41 | 30 | 62 | 10 |
| 6 | 12 | 50 | 34 | 100 | 57 | 50 |

Adjuvant arthritis (Test 4)

The investigations were carried out by the method of Pearson (Arthrit. Rheum., Vol. 2, (1959) p. 44). The experimental animals used were male rats of a Wistar-Lewis strain having a body weight between 130 to 200 g. The compounds to be tested were administered orally once daily for 12 days, starting on the day of immunization. The animals of a control group received only the vehicle. Each preparation and control group comprised 6 animals. The criterion used to determine activity was the percentage reduction in the increase in paw volume compared to that of the untreated control group.

Reverse Passive Arthus Reaction (Test 5)

One hour before challenge, test compounds were administered orally to male or female Wistar rats weighing 120–200 g. After this pre-treatment period, the reaction was induced by a subplantar injection of goat anti-rat serum in the right hind paw. The left hind paw, which served as a control, was injected with saline alone. Paw volumes were determined immediately and four hours after antibody challenge. The results of these tests are given in Table III. Doses are given in units of mg/kg p.o.

TABLE III

| | Test 4 | | Test 5 | |
|---|---|---|---|---|
| Example | Dose | % inhibition | Dose | % inhibition |
| 1 | 25 | −16 | 50 | 42 |
| | | | 100 | 26 |

TABLE III-continued

| | Test 4 | | Test 5 | |
|---|---|---|---|---|
| Example | Dose | % inhibition | Dose | % inhibition |
| 2 | 25 | 92 | 50 | −9 |
| | | | 100 | 27 |
| 3 | 25 | 90 | 50 | 41 |
| | | | 100 | 36 |
| 4 | 25 | 22 | 50 | 17 |
| | | | 100 | 28 |
| 5 | 25 | 88 | 50 | 23 |
| | | | 100 | 34 |
| 6 | 25 | 42 | 50 | 24 |
| | | | 100 | 38 |

KINETIC DATA

A comparison was made between a known compound, namely 5-cyclopropyl-N-(4-trifluoromethylphenyl)-isoxazole-4-carboxamide and the compounds of the present invention, namely compounds of Examples 5 and 6 above. The compounds were administered orally to mice at doses of 30 mg/kg and plasma concentrations were monitored for 72 hours. The results show the appropriate metabolic half-life for the known compound to be approximately 21.4 hours whereas that for both of the compounds of Examples 5 and 6 of the invention was about one third of this value, namely 7.1 hours (Ex. 5) and 8.2 hours (Ex. 6).

These results demonstrate the kinetic advantage conferred by the presence of the methyl group as the $R_5$ substituent in the compounds of the invention.

Various modifications of the compounds and method may be made without departing from the spirit or scope of the invention and it is to be understood that the invention is intended to be limited only as defined in the appended claims.

We claim:

1. A compound selected from the group consisting of a compound of the formula

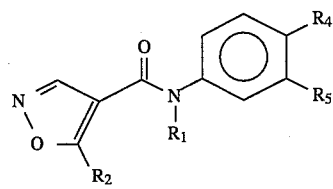

wherein $R_1$ is hydrogen or alkyl of 1 to 3 carbon atoms; $R_2$ is cycloalkyl of 3 to 6 carbon atoms; $R_4$ is selected from the group consisting of nitrile and nitro, and $R_5$ is hydrogen and their non-toxic pharmaceutically acceptable salts.

2. A compound of claim 1 wherein $R_1$ is hydrogen and $R_2$ is cyclopropyl.

3. An anti-inflammatory composition comprising an anti-inflammatorily effective amount of a compound of claim 1 and an inert pharmaceutical carrier.

4. A composition of claim 3 wherein $R_1$ is hydrogen and $R_2$ is cyclopropyl.

5. A method of relieving inflammation in warm-blooded animals comprising administering to warm-blooded animals an anti-inflammatorily effective amount of a compound of claim 1.

6. A method of claim 5 wherein $R_1$ is hydrogen and $R_2$ is cyclopropyl.

7. A compound of claim 1 selected from the group consisting of 5-cyclopropyl-N-(4-cyanophenyl)-isoxazole-4-carboxamide; 5-cyclopropyl-N-( 4-nitrophenyl)-isoxazole-4-carboxamide and their non-toxic pharmaceutically acceptable salts.

8. A composition of claim 3 wherein the compound is selected from the group consisting of 5-cyclopropyl-N-(4-cyanophenyl)-isoxazole-4-carboxamide; 5-cyclopropyl-N-(4-nitrophenyl)-isoxazole-4-carboxamide and their non-toxic pharmaceutically acceptable salts.

9. A method of claim 5 wherein the compound is selected from the group consisting of 5-cyclopropyl-N-(4-cyanophenyl)-isoxazole-4-carboxamide; 5-cyclopropyl-N-(4nitrophenyl)-isoxazole-4-carboxamide and their non-toxic pharmaceutically acceptable salts.

* * * * *